(12) United States Patent
Deuerlein et al.

(10) Patent No.: US 9,376,457 B2
(45) Date of Patent: Jun. 28, 2016

(54) HYDROPHOBIC, FUNCTIONALIZED PARTICLES

(75) Inventors: Stephan Deuerlein, Ludwigshafen (DE); Imme Domke, Mannheim (DE); Alexej Michailovski, Ludwigshafen (DE); Reinhold Rieger, Offstein (DE); Piyada Charoensirisomboon, Mannheim (DE); Christian Eichholz, Mannheim (DE); Robert Bayer, Sinsheim (DE)

(73) Assignee: BASF SE, Ludwigshafen (DE)

( * ) Notice: Subject to any disclaimer, the term of this patent is extended or adjusted under 35 U.S.C. 154(b) by 1028 days.

(21) Appl. No.: 13/225,046

(22) Filed: Sep. 2, 2011

(65) Prior Publication Data

US 2012/0058463 A1 Mar. 8, 2012

Related U.S. Application Data

(60) Provisional application No. 61/379,744, filed on Sep. 3, 2010.

(51) Int. Cl.
*C07F 7/18* (2006.01)
*H01F 1/00* (2006.01)

(52) U.S. Cl.
CPC .......... *C07F 7/1836* (2013.01); *H01F 1/0054* (2013.01); *C07B 2200/11* (2013.01)

(58) Field of Classification Search
CPC .. C07F 7/1836; H01F 1/0054; C07B 2200/11
USPC ............. 252/62.51 R, 62.56, 62.59; 556/5, 9, 556/400, 463
See application file for complete search history.

(56) References Cited

U.S. PATENT DOCUMENTS

| 7,196,043 B2 * | 3/2007 | Valpey et al. .................. 510/204 |
| 9,024,050 B2 * | 5/2015 | Deuerlein et al. ............ 556/400 |
| 2011/0163278 A1 | 7/2011 | Domke et al. |
| 2011/0240527 A1 | 10/2011 | Domke et al. |
| 2011/0272623 A1 | 11/2011 | Domke et al. |
| 2011/0303772 A1 | 12/2011 | Michailovski et al. |
| 2011/0303773 A1 | 12/2011 | Domke et al. |
| 2011/0309003 A1 | 12/2011 | Domke et al. |
| 2012/0000857 A1 | 1/2012 | Domke et al. |
| 2012/0264111 A1 * | 10/2012 | Deuerlein et al. ..... 252/62.51 R |
| 2012/0302786 A1 | 11/2012 | Stroefer et al. |

FOREIGN PATENT DOCUMENTS

| AU | 2003210151 A1 | 7/2003 |
| WO | WO 03/058649 A1 | 7/2003 |
| WO | WO 2006105600 A1 * | 10/2006 |
| WO | WO 2009/059382 A1 | 5/2009 |
| WO | WO 2010/097361 A1 | 9/2010 |
| WO | WO 2010/100180 A1 | 9/2010 |
| WO | WO 2010/100181 A1 | 9/2010 |
| WO | WO 2011/012539 A1 | 2/2011 |
| WO | WO 2011/058033 A1 | 5/2011 |
| WO | WO 2011/058039 A1 | 5/2011 |
| WO | WO 2011/064757 A1 | 6/2011 |
| WO | WO 2012028701 A2 * | 3/2012 |

OTHER PUBLICATIONS

International Search Report for PCT/EP2011/065162, Mar. 2012.*
Written Opinion for PCT/EP2011/065162, Mar. 2012.*
Translation of the International Preliminary Report on Patentability for PCT/EP2011/065162, Mar. 2013.*
Sigma-Aldrich commmerically available Zinc Oxide composition, first mentioned in a peer review paper dated 1999.*
International Search Report and Written Opinion issued Mar. 2, 2012 in patent application No. PCT/EP2011/065162 with English Translation of Category of Cited Documents.

* cited by examiner

*Primary Examiner* — David A Reifsnyder
(74) *Attorney, Agent, or Firm* — Oblon, McClelland, Maier & Neustadt, L.L.P.

(57) ABSTRACT

The present invention relates to a stable mixture comprising surface-modified particles which are obtained by reacting metal oxide or semimetal oxide particles with at least one compound selected from among silicon-comprising compounds bearing one, two or three alkoxy radicals and at least one solvent, at least one surface-active substance or a mixture thereof, the use of these particles in systems in which they are brought into contact with at least one solvent, where the mass ratio of solvent to modified particle is greater than 500, and also the use of these particles in agglomeration-deagglomeration cycles.

17 Claims, No Drawings

HYDROPHOBIC, FUNCTIONALIZED PARTICLES

The present invention relates to a stable mixture comprising surface-modified particles which are obtained by reacting metal oxide or semimetal oxide particles with at least one compound selected from among silicon-comprising compounds bearing one, two or three alkoxy radicals and at least one solvent, at least one surface-active substance or a mixture thereof, the use of these particles in systems in which they are brought into contact with at least one solvent, where the mass ratio of solvent to modified particle is greater than 500, and also the use of these particles in agglomeration-deagglomeration cycles.

Metal oxide and/or semimetal oxide particles which are functionalized on the surface by means of silicon-comprising compounds are known from the prior art.

WO 2009/059382 A1 discloses, for example, hydrophobic modification of mineral fillers and mixed polymer systems. According to this document, hydrophobic modification is effected by reaction of the corresponding mineral particles with silanes, for example $C_3$-$C_{12}$-alkyltrialkoxy silanes. That the correspondingly hydrophobically modified particles according to WO 2009/059382 A1 are particularly stable in large amounts of solvents, optionally in the presence of surface-active substances, is not disclosed in this document.

In the light of the prior art, it is thus an object of the present invention to provide particles which are hydrophobicized on the surface and have a particularly high stability toward large amounts of solvents and/or surface-active substances.

This object is achieved by a stable mixture comprising surface-modified particles which are obtained by reacting metal oxide or semimetal oxide particles with at least one compound of the general formula (I)

$$R^1{}_n\text{—Si}(OR^2)_{4-n} \qquad (I)$$

or polysiloxanes of the general formula (II)

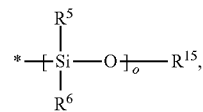
(II)

where $R^1$, $R^2$, $R^3$, $R^4$, $R^9$, $R^{10}$, a, b, m and n have the following meanings:

$R^1$, $R^2$,
$R^9$, $R^{10}$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, the radicals $R^3$ are each, independently of one another, hydrogen, linear or branched, optionally functionalized $C_1$-$C_{30}$-alkyl, linear or branched, optionally functionalized $C_2$-$C_{20}$-alkenyl, linear or branched, optionally functionalized $C_2$-$C_{20}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, —$OR^{17}$, a unit of the general formula

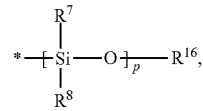

the radicals $R^4$ are each, independently of one another, hydrogen, linear or branched, optionally functionalized $C_1$-$C_{30}$-alkyl, linear or branched, optionally functionalized $C_2$-$C_{20}$-alkenyl, linear or branched, optionally functionalized $C_2$-$C_{20}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, —$OR^{18}$, a unit of the general formula

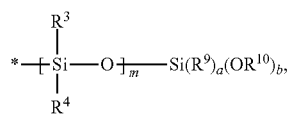

$R^5$, $R^6$,
$R^7$, $R^8$, are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, the radicals $R^{15}$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, or a unit of the general formula

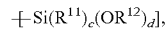

the radicals $R^{16}$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, or a unit of the general formula

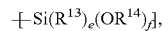

$R^{11}$, $R^{12}$,
$R^{13}$, $R^{14}$, $R^{17}$, $R^{18}$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, n is 1, 2 or 3, a, c, e are each, independently of one another, 0, 1 or 2, preferably 0, b is 3-a, d is 3-c, f is 3-e and m, o, p are each, independently of one another, from 1 to 500, preferably from 1 to 50, particularly preferably from 1 to 20, and at least one solvent, at least one surface-active substance or a mixture thereof.

According to the present invention polysiloxanes according to general formula (II) are polysiloxanes comprising units of general formula (II). The bonding is therein conducted via the *marked bonding respectively via a valid bonding at the Si-atom.

The present invention further relates to a stable mixture comprising surface-modified particles which are obtained by reacting metal oxide or semi-metal oxide particles with at least one compound of general formula (I)

$$R^1{}_n\text{---}Si(OR^2)_{4-n} \qquad (I)$$

wherein $R^1$, $R^2$ and n have the following meanings:

$R^1$ independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, $R^2$ independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, and/or group of general formula (IIa)

$$\text{---}SiR^1{}_m(OR^2)_{3-m} \qquad (IIa)$$

wherein $R^1$ and $R^2$ independently of one another have the above-mentioned meanings and m is independently of one another 0, 1, 2 or 3 n 1, 2 or 3 and at least one solvent, at least one surface active substance or a mixture thereof.

If $R^2$ in the compound of general formula (I) has several times, for example more than once, the meaning of a group of general formula (IIa), corresponding compounds are present, comprising 2, 3, 4 or more units with Si-atoms. According to this, in the case, that in general formula (I) $R^2$ is several times a group of general formula (IIa), polysiloxanes are present, corresponding to general formula (II).

Furthermore, the object is achieved by the use of the surface-modified particle according to the invention in systems in which the modified particles are brought into contact with at least one solvent, where the mass ratio of solvent to modified particle is greater than 500.

The object of the invention is also achieved by the use of surface-modified particles according to the invention in agglomeration-deagglomeration cycles.

The stable mixture of the invention comprises surface-modified particles which are obtained by reacting metal oxide or semimetal oxide particles with at least one compound of the general formula (I), a polysiloxane of the general formula (II), or a compound of general formula (I) comprising groups of general formula (IIa), which preferably define polysiloxanes, too.

For the purposes of the present invention, it is generally possible to use all metal oxide or semimetal oxide particles, in particular metal oxide particles, known to those skilled in the art. Examples of metal oxides which are particularly suitable for the purposes of the invention are the oxides of the metals of the main groups and transition groups of the Periodic Table of the Elements, in particular the transition groups of the Periodic Table of the Elements.

According to the invention, silicon oxide is not preferred as semimetal oxide and is therefore not comprised in a preferred embodiment of the present invention.

In a preferred embodiment, the present invention therefore provides the mixture according to the invention, with silicon dioxide being excepted as semimetal oxide.

Examples of suitable metals of the main groups of the Periodic Table of the Elements are the alkali metals, for example Li, Na, K, Rb, Cs, alkaline earth metals, for example Be, Mg, Ca, Ba, Sr, the third main group of the Periodic Table of the Elements, for example Al, Ga, In, Tl, the fourth main group of the Periodic Table of the Elements, for example Sn, Pb, or the fifth main group of the Periodic Table of the Elements, for example Sb, Bi.

Examples of suitable metals of the transition groups of the Periodic Table of the Elements are Sc, Y, the lanthanides, the actinides, Ti, Zr, Hf, Mn, Re, Fe, Ru, Os, Co, Rh, Ir, Ni, Pd, Pt, Cu, Ag, Au, Zn and Cd.

In a preferred embodiment, the metal oxide used according to the invention is an oxide of the metals selected from the group consisting of Li, Na, K, Rb, Cs, Be, Mg, Ca, Ba, Sr, Al, Ga, In, Tl, Sn, Pb, Sb, Bi, Sc, Y, the lanthanides, the actinides, Ti, Zr, Hf, Mn, Re, Fe, Ru, Os, Co, Rh, Ir, Ni, Pd, Pt, Cu, Ag, Au, Zn, Cd and mixtures thereof, very particularly preferably selected from the group consisting of Mn, Fe, Co, Ni, Cu and combinations thereof. Furthermore, mixed oxides of these metals, in particular Mn, Fe, Co, Ni or Cu, with at least one alkaline earth metal, for example Mg, Ca, Sr and/or Ba, are also suitable for the purposes of the invention.

The present invention therefore preferably provides the mixture of the invention in which the metal oxide used is an oxide of a metal selected from the group consisting of Mn, Fe, Co, Ni, Cu, combinations thereof and mixed oxides of these metals with at least one alkaline earth metal, for example Mg, Ca, Sr and/or Ba.

In a particularly preferred embodiment, the present invention provides the mixture of the invention in which the metal oxide or semimetal oxide particles are magnetic.

Very particularly preferably preferred metal oxides are iron oxides, for example $Fe_2O_3$, magnetic iron oxides, for example magnetite, maghemite, hematite, cubic ferrites of the general formula (III)

$$M^{2+}{}_xFe^{2+}{}_{1-x}Fe^{3+}{}_2O_4 \quad \text{(III)}$$

where
M is selected from among Co, Ni, Mn, Zn and mixtures thereof and
x is ≤1,
hexagonal ferrites, for example calcium, barium or strontium ferrite $MFe_6O_{19}$ where M=Ca, Sr, Ba, and combinations thereof.

In a preferred embodiment, the metal oxide used according to the invention is a magnetic iron oxide selected from the abovementioned group. In a very particularly preferred embodiment, the at least one metal oxide used according to the invention is magnetite. Magnetite has the formula $Fe_3O_4$, in particular $Fe^{II}Fe^{III}{}_2O_4$, and is known to those skilled in the art. Magnetite can be prepared by known processes and is commercially available.

The metal oxide particles used according to the invention can optionally comprise dopants, for example further metals in oxidic or elemental form, for example noble metals such as platinum.

The particles which are present according to the invention generally have a particle size of from 50 nm to 500 μm, preferably from 200 nm to 100 μm, particularly preferably from 500 nm to 10 μm.

The particles which are present according to the invention can generally have any shape, for example spherical, cylindrical, acicular or cuboidal.

Surface-modified particles which are obtained by reacting metal oxide or semimetal oxide particles with at least one compound of the general formula (I)

$$R^1{}_n\text{—}Si(OR^2)_{4-n} \quad \text{(I)}$$

or polysiloxanes of the general formula (II)

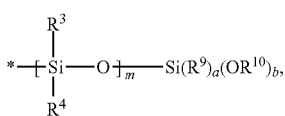

where $R^1$, $R^2$, $R^3$, $R^4$, $R^9$, $R^{10}$, a, b, m and n have the abovementioned meaning, are present in the stable mixture of the invention.

Preference is given to the radicals $R^1$ each being, independently of one another, linear or branched, optionally functionalized $C_1$-$C_{30}$-alkyl, particularly preferably $C_1$-$C_{20}$-alkyl, very particularly preferably $C_4$-$C_{12}$-alkyl. In a preferred embodiment, $R^1$ is linear or branched, unfunctionalized $C_1$-$C_{30}$-alkyl, particularly preferably $C_1$-$C_{20}$-alkyl, very particularly preferably $C_4$-$C_{12}$-alkyl. Examples of linear or branched $C_4$-$C_{12}$-alkyl radicals are butyl, in particular, n-butyl, isobutyl, tert-butyl, pentyl, in particular n-pentyl, isopentyl, tert-pentyl, hexyl, in particular n-hexyl, isohexyl, tert-hexyl, heptyl, in particular n-heptyl, isoheptyl, tert-heptyl, octyl, in particular n-octyl, isooctyl, tert-octyl, nonyl, in particular n-nonyl, isononyl, tert-nonyl, decyl, in particular n-decyl, isodecyl, tert-decyl, undecyl, in particular n-undecyl, isoundecyl, tert-undecyl, or dodecyl, in particular n-dodecyl, isododecyl, tert-dodecyl.

Further preference is given to the radicals $R^1$ each being, independently of one another, linear or branched, optionally functionalized $C_2$-$C_{30}$-alkenyl, particularly preferably $C_2$-$C_{20}$-alkenyl, very particularly preferably $C_4$-$C_{12}$-alkenyl. Examples of alkenyl radicals which are particularly preferred according to the invention are ethenyl (vinyl), propenyl, in particular n-propenyl, isopropenyl, butenyl, in particular n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl, tert-dodecenyl.

Further preference is given to the radicals $R^1$ each being, independently of one another, linear or branched, optionally functionalized $C_2$-$C_{30}$-alkynyl, particularly preferably $C_2$-$C_{20}$-alkynyl, very particularly preferably $C_4$-$C_{12}$-alkynyl. Examples of alkynyl radicals which are particularly preferred according to the invention are ethynyl, propynyl, in particular n-propynyl, isopropynyl, butynyl, in particular n-butynyl, isobutynyl, tert-butynyl, pentynyl, in particular n-pentynyl, isopentynyl, tert-pentynyl, hexynyl, in particular n-hexynyl, isohexynyl, tert-hexynyl, heptynyl, in particular n-heptynyl, isoheptynyl, tert-heptynyl, octynyl, in particular n-octynyl, isooctynyl, tert-octynyl, nonynyl, in particular n-nonynyl, isononynyl, tert-nonynyl, decynyl, in particular n-decynyl, isodecynyl, tert-decynyl, undecynyl, in particular n-undecynyl, isoundecynyl, tert-undecynyl, or dodecynyl, in particular n-dodecynyl, isododecynyl, tert-dodecynyl.

Further preference is given to the radicals $R^1$ each being, independently of one another, optionally functionalized $C_3$-$C_{20}$-cycloalkyl, particularly preferably $C_3$-$C_{12}$-cycloalkyl, very particularly preferably $C_3$-$C_6$-cycloalkyl, for example cyclopropyl, cyclobutyl, cyclopentyl, cyclohexyl.

Further preference is given to the radicals $R^1$ each being, independently of one another, optionally functionalized $C_3$-$C_{20}$-cycloalkenyl, particularly preferably $C_3$-$C_{12}$-cycloalkenyl, very particularly preferably $C_3$-$C_6$-cycloalkenyl, for example cyclopropenyl, cyclobutenyl, cyclopentenyl, cyclohexenyl.

Further preference is given to the radicals $R^1$ each being, independently of one another, optionally functionalized $C_1$-$C_{20}$-heteroalkyl, particularly preferably $C_1$-$C_{12}$-heteroalkyl. The heteroalkyl radicals present according to the invention are derived from the abovementioned alkyl radicals, with at least one carbon atom being replaced by a heteroatom selected from among N, O, P and S.

Further preference is given to the radicals $R^1$ each being, independently of one another, optionally functionalized $C_5$-$C_{22}$-aryl, particularly preferably $C_5$-$C_{12}$-aryl. Examples of aryl radicals which are preferred according to the invention are phenyl, naphthyl or biaryls.

Further preference is given to the radicals $R^1$ each being, independently of one another, optionally functionalized $C_6$-$C_{23}$-alkylaryl, particularly preferably $C_6$-$C_{13}$-alkylaryl. An example of an alklaryl radical which is preferred according to the invention is benzyl.

Further preference is given to the radicals $R^1$ each being, independently of one another, optionally functionalized $C_6$-$C_{23}$-arylalkyl, particularly preferably $C_6$-$C_{13}$-arylalkyl. Examples of arylalkyl radicals which are preferred according to the invention are tolyl, xylyl, propylbenzyl, hexylbenzyl.

Further preference is given to the radicals $R^1$ each being, independently of one another, optionally functionalized $C_5$-$C_{22}$-heteroaryl, particularly preferably $C_6$-$C_{12}$-heteroaryl.

The abovementioned radicals $R^1$ can optionally be functionalized. Suitable functional groups are, for example, selected from among amino, amido, imido, hydroxyl, ether, aldehyde, keto, carboxylic acid, thiol, thioether, hydroxamate and carbamate groups. The abovementioned radicals $R^1$ can be singly or multiply functionalized. In the case of multiple functionalization, one functional group can be present a plurality of times or various functional groups are simultaneously present. The radicals mentioned for $R^1$ can also be monosubstituted or polysubstituted by the abovementioned alkyl, alkenyl, alkynyl, aryl, alkylaryl, arylalkyl, heteroalkyl or heteroaryl radicals.

Very particularly preferred radicals $R^1$ are octyl, in particular n-octyl, hexyl, in particular n-hexyl and/or butyl, in particular n-butyl, decyl, in particular n-decyl, or dodecyl, in particular n-dodecyl.

For the purposes of the present invention, "independently of one another" means that if a plurality of radicals $R^1$ are present in the compound of the general formula (I), these can be identical or different.

Preference is given to the radicals $R^2$ each being, independently of one another, linear or branched, optionally functionalized $C_1$-$C_{30}$-alkyl, particularly preferably $C_1$-$C_{20}$-alkyl, very particularly preferably $C_1$-$C_{12}$-alkyl. In a preferred embodiment, $R^2$ is linear or branched, unfunctionalized $C_1$-$C_{30}$-alkyl, particularly preferably $C_1$-$C_{20}$-alkyl, very particularly preferably $C_1$-$C_{12}$-alkyl. Examples of linear or branched $C_1$-$C_{12}$-alkyl radicals are methyl, ethyl, propyl, in particular n-propyl, isopropyl, butyl, in particular n-butyl, isobutyl, tert-butyl, pentyl, in particular n-pentyl, isopentyl, tert-pentyl, hexyl, in particular n-hexyl, isohexyl, tert-hexyl, heptyl, in particular n-heptyl, isoheptyl, tert-heptyl, octyl, in particular n-octyl, isooctyl, tert-octyl, nonyl, in particular n-nonyl, isononyl, tert-nonyl, decyl, in particular n-decyl, isodecyl, tert-decyl, undecyl, in particular n-undecyl, isoundecyl, tert-undecyl, or dodecyl, in particular n-dodecyl, isododecyl, tert-dodecyl.

Further preference is given to the radicals $R^2$ each being, independently of one another, linear or branched, optionally functionalized $C_2$-$C_{30}$-alkenyl, particularly preferably $C_2$-$C_{20}$-alkenyl, very particularly preferably $C_2$-$C_{12}$-alkenyl. Examples of alkynyl radicals which are particularly preferred according to the invention are ethenyl (vinyl), propenyl, in particular n-propenyl, isopropenyl, butenyl, in particular n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl, tert-dodecenyl.

Further preference is given to the radicals $R^2$ each being, independently of one another, linear or branched, optionally functionalized $C_2$-$C_{30}$-alkynyl, particularly preferably $C_2$-$C_{20}$-alkynyl, very particularly preferably $C_2$-$C_{12}$-alkynyl. Examples of alkynyl radicals which are particularly preferred according to the invention are ethynyl, propynyl, in particular n-propynyl, isopropynyl, butynyl, in particular n-butynyl, isobutynyl, tert-butynyl, pentynyl, in particular n-pentynyl, isopentynyl, tert-pentynyl, hexynyl, in particular n-hexynyl, isohexynyl, tert-hexynyl, heptynyl, in particular n-heptynyl, isoheptynyl, tert-heptynyl, octynyl, in particular n-octynyl, isooctynyl, tert-octynyl, nonynyl, in particular n-nonynyl, isononynyl, tert-nonynyl, decynyl, in particular n-decynyl, isodecynyl, tert-decynyl, undecynyl, in particular n-undecynyl, isoundecynyl, tert-undecynyl, or dodecynyl, in particular n-dodecynyl, isododecynyl, tert-dodecynyl.

Further preference is given to the radicals $R^2$ each being, independently of one another, optionally functionalized $C_3$-$C_{20}$-cycloalkyl, particularly preferably $C_3$-$C_{12}$-cycloalkyl, particularly preferably $C_3$-$C_6$-cycloalkyl, for example cyclopropyl, cyclobutyl, cyclopentyl, cyclohexyl.

Further preference is given to the radicals $R^2$ each being, independently of one another, optionally functionalized $C_3$-$C_{20}$-cycloalkenyl, particularly preferably $C_3$-$C_{12}$-cycloalkenyl, very particularly preferably $C_3$-$C_6$-cycloalkenyl, for example cyclopropenyl, cyclobutenyl, cyclopentenyl, cyclohexenyl.

Further preference is given to the radicals $R^2$ each being, independently of one another, optionally functionalized $C_1$-$C_{20}$-heteroalkyl, particularly preferably $C_4$-$C_{12}$-heteroalkyl. The heteroalkyl radicals which are present according to the invention are derived from the abovementioned alkyl radicals, with at least one carbon atom being replaced by a heteroatom selected from among N, O, P and S.

Further preference is given to the radicals $R^2$ each being, independently of one another, optionally functionalized $C_5$-$C_{22}$-aryl, particularly preferably $C_5$-$C_{12}$-aryl. Examples of aryl radicals which are preferred according to the invention are phenyl, naphthyl or biaryls.

Further preference is given to the radicals $R^2$ each being, independently of one another, optionally functionalized $C_6$-$C_{23}$-alkylaryl, particularly preferably $C_6$-$C_{13}$-alkylaryl. An example of an alkylaryl radical which is preferred according to the invention is benzyl.

Further preference is given to the radicals $R^2$ each being, independently of one another, optionally functionalized $C_6$-$C_{23}$-arylalkyl, particularly preferably $C_6$-$C_{13}$-arylalkyl. Examples of arylalkyl radicals which are preferred according to the invention are tolyl, xylyl, propylbenzyl, hexylbenzyl.

Further preference is given to the radicals $R^2$ each being, independently of one another, optionally functionalized $C_5$-$C_{22}$-heteroaryl, particularly preferably $C_5$-$C_{12}$-heteroaryl.

The abovementioned radicals $R^2$ can optionally be functionalized. Suitable functional groups are, for example, selected from among amino, amido, imido, hydroxy, ether, aldehyde, keto, carboxylic acid, thiol, thioether, hydroxamate and carbamate groups. The abovementioned radicals $R^1$ can be singly or multiply functionalized. In the case of multiple functionalization, one functional group can be present a plurality of times or various functional groups are simultaneously present. The radicals mentioned for $R^2$ can also be monosubstituted or polysubstituted by the abovementioned alkyl, alkenyl, alkynyl, aryl, alkylaryl, arylalkyl, heteroalkyl or heteroaryl radicals.

Very particularly preferred radicals $R^2$ are methyl and/or ethyl.

The present invention therefore preferably provides the mixture of the invention in which $R^2$ in the compound of the general formula (I) is methyl or ethyl.

In a further preferred embodiment $R^2$ is a group of general formula (IIa)

$$-SiR^1{}_m(OR^2)_{3-n} \qquad (IIa)$$

wherein $R^1$ and $R^2$ independently of one another have the above-mentioned meanings and m is independently of one another 0, 1, 2 or 3, preferably 1 or 2. The connection of this group of general formula (IIa) to the compound of general formula (I) is via the free bonding at the Si-atom.

In a preferred embodiment $R^1$ in the group of general formula (IIa) is independently of one another octyl, preferably n-octyl, hexyl, preferably n-hexyl and/or -butyl, preferably n-butyl, decyl, preferably n-decyl or docecyl, preferably n-dodecyl.

In a particularly preferred embodiment $R^2$ is in the group of general formula (IIa) independently of one another methyl or ethyl.

Therefore, the present invention preferably relates to the mixture according to the present invention, wherein in the compound of general formula (I) or in the group of general formula (IIa) $R^2$ is methyl or ethyl.

If in the compound of general formula (I) groups of general formula (IIa) are present several times, according to the present invention polysiloxanes are used as compounds of general formula (I). If according to the present invention polysiloxanes comprising groups of general formula (IIa) are used, these can be linear or branched. Polysiloxanes which are used according to the present invention comprising groups of the general formula (IIa) have in general a molecular weight of 250 to 200,000 g/mol, preferably 250 to 20,000 g/mol, particularly preferably 300 to 5,000 g/mol.

For the purposes of the present invention, "independently of one another" means that if a plurality of radicals $R^2$ are present in the compound of the general formula (I), these can be identical or different.

Preference is given to the radicals $R^3$ each being, independently of one another, linear or branched, optionally functionalized $C_1$-$C_{30}$-alkyl, particularly preferably $C_1$-$C_{20}$-alkyl, very particularly preferably $C_1$-$C_{12}$-alkyl. In a preferred embodiment, $R^3$ is linear or branched, unfunctionalized $C_1$-$C_{30}$-alkyl, particularly preferably $C_1$-$C_{20}$-alkyl, very particularly preferably $C_1$-$C_{12}$-alkyl. Examples of linear or branched $C_1$-$C_{12}$-alkyl radicals are methyl, ethyl, propyl, in particular n-propyl, isopropyl, butyl, in particular n-butyl, isobutyl, tert-butyl, pentyl, in particular n-pentyl, isopentyl, tert-pentyl, hexyl, in particular n-hexyl, isohexyl, tert-hexyl, heptyl, in particular n-heptyl, isoheptyl, tert-heptyl, octyl, in particular n-octyl, isooctyl, tert-octyl, nonyl, in particular n-nonyl, isononyl, tert-nonyl, decyl, in particular n-decyl, isodecyl, tert-decyl, undecyl, in particular n-undecyl, isoundecyl, tert-undecyl, or dodecyl, in particular n-dodecyl, isododecyl, tert-dodecyl.

Further preference is given to the radicals $R^3$ each being, independently of one another, linear or branched, optionally functionalized $C_2$-$C_{30}$-alkenyl, particularly preferably $C_2$-$C_{20}$-alkenyl, very particularly preferably $C_2$-$C_{12}$-alkenyl. Examples of alkenyl radicals which are particularly preferred according to the invention are ethenyl (vinyl), propenyl, in particular n-propenyl, isopropenyl, butenyl, in particular n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl, tert-dodecenyl.

Further preference is given to the radicals $R^3$ each being, independently of one another, linear or branched, optionally functionalized $C_2$-$C_{30}$-alkynyl, particularly preferably $C_2$-$C_{20}$-alkynyl, very particularly preferably $C_2$-$C_{12}$-alkynyl. Examples of alkynyl radicals which are particularly preferred according to the invention are ethynyl, propynyl, in particular n-propynyl, isopropynyl, butynyl, in particular n-butynyl, isobutynyl, tert-butynyl, pentynyl, in particular n-pentynyl, isopentynyl, tert-pentynyl, hexynyl, in particular n-hexynyl, isohexynyl, tert-hexynyl, heptynyl, in particular n-heptynyl, isoheptynyl, tert-heptynyl, octynyl, in particular n-octynyl, isooctynyl, tert-octynyl, nonynyl, in particular n-nonynyl, isononynyl, tert-nonynyl, decynyl, in particular n-decynyl, isodecynyl, tert-decynyl, undecynyl, in particular n-undecynyl, isoundecynyl, tert-undecynyl, or dodecenyl, in particular n-dodecynyl, isododecynyl, tert-dodecynyl.

Further preference is given to the radicals $R^3$ each being, independently of one another, optionally functionalized $C_3$-$C_{20}$-cycloalkyl, particularly preferably $C_3$-$C_{12}$-cycloalkyl, particularly preferably $C_3$-$C_6$-cycloalkyl, for example cyclopropyl, cyclobutyl, cyclopentyl, cyclohexyl.

Further preference is given to the radicals $R^3$ each being, independently of one another, optionally functionalized $C_3$-$C_{20}$-cycloalkenyl, particularly preferably $C_3$-$C_{12}$-cycloalkenyl, very particularly preferably $C_3$-$C_6$-cycloalkenyl, for example cyclopropenyl, cyclobutenyl, cyclopentenyl, cyclohexenyl.

Further preference is given to the radicals $R^3$ each being, independently of one another, optionally functionalized $C_1$-$C_{20}$-heteroalkyl, particularly preferably $C_1$-$C_{12}$-heteroalkyl. The heteroalkyl radicals which are present according to the invention are derived from the abovementioned alkyl radicals, with at least one carbon atom being replaced by a heteroatom selected from among N, O, P and S.

Further preference is given to the radicals $R^3$ each being, independently of one another, optionally functionalized $C_5$-$C_{22}$-aryl, particularly preferably $C_5$-$C_{12}$-aryl. Examples of aryl radicals which are preferred according to the invention are phenyl, naphthyl, biaryls.

Further preference is given to the radicals $R^3$ each being, independently of one another, optionally functionalized $C_6$-$C_{23}$-alkylaryl, particularly preferably $C_6$-$C_{13}$-alkylaryl. An example of an alkylaryl radical which is preferred according to the invention is benzyl.

Further preference is given to the radicals $R^3$ each being, independently of one another, optionally functionalized $C_6$-$C_{23}$-arylalkyl, particularly preferably $C_6$-$C_{13}$-arylalkyl. Examples of arylalkyl radicals which are preferred according to the invention are tolyl, xylyl, propylbenzyl, hexylbenzyl.

Further preference is given to the radicals $R^3$ each being, independently of one another, optionally functionalized $C_5$-$C_{22}$-heteroaryl, particularly preferably $C_5$-$C_{12}$-heteroaryl.

$R^3$ can, in one embodiment, be —$OR^{17}$, where $R^{17}$ has the abovementioned meanings. In one possible embodiment, possible and preferred embodiments of $R^{17}$ correspond, independently of one another, to the possible and preferred embodiments mentioned for $R^2$. In this embodiment, $R^{17}$ is very particularly preferably selected from among methyl, ethyl, hexyl, octyl, decyl, dodecyl. When $R^3$ is —$OR^{17}$, crosslinked siloxane structures are formed in the modification of the particle surface.

In a further preferred embodiment of the present invention, $R^3$ is a unit of the general formula

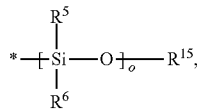

where $R^5$, $R^6$, $R^{15}$ and o have the above-mentioned meanings.

The preferred embodiments of $R^5$ and $R^6$ correspond, independently of one another, to the possible and preferred embodiments mentioned for $R^2$. $R^5$ and $R^6$ are very particularly preferably selected independently from among methyl, ethyl, hexyl, octyl, decyl, dodecyl.

In one possible embodiment, possible and preferred embodiments of $R^{15}$ correspond, independently of one another, to the possible and preferred embodiments mentioned for $R^2$. In this embodiment, $R^{15}$ is very particularly preferably selected from among methyl, ethyl.

In a further embodiment according to the invention, $R^{15}$ can be a unit of the general formula

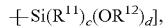

where $R^{11}$, $R^{12}$, c and d have the above-mentioned meanings.

In one possible embodiment, possible and preferred embodiments of $R^{11}$ correspond, independently of one another, to the possible and preferred embodiments mentioned for $R^2$. In this embodiment, $R^{11}$ is very particularly preferably selected from among methyl, ethyl, hexyl, octyl, decyl, dodecyl.

In one possible embodiment, possible and preferred embodiments of $R^{12}$ correspond, independently of one another, to the possible and preferred embodiments mentioned for $R^2$. In this embodiment, $R^{12}$ is very particularly preferably selected from among methyl, ethyl.

The indices c are each, independently of one another, 0, 1 or 2, preferably 0.

d is 3-c, i.e. d can assume the values 1, 2, or 3, with 3 being preferred.

The abovementioned radicals $R^3$ can optionally be functionalized. Suitable functional groups are, for example, selected from among amino, amido, imido, hydroxy, ether, aldehyde, keto, carboxylic acid, thiol, thioether, hydroxamate and carbamate groups. The abovementioned radicals $R^1$ can be singly or multiply functionalized. In the case of multiple functionalization, one functional group can be present a plurality of times or various functional groups are simultaneously present. Furthermore, the radicals mentioned for $R^1$ can also be monosubstituted or polysubstituted by the abovementioned alkyl, alkenyl, alkynyl, aryl, alkylaryl, arylalkyl, heteroalkyl or heteroaryl radicals.

Very particularly preferred radicals $R^3$ are methyl, butyl, in particular n-butyl, hexyl, in particular n-hexyl, octyl, in particular n-octyl, decyl, in particular n-decyl and dodecyl, in particular n-dodecyl.

For the purposes of the present invention, "independently of one another" means that if a plurality of radicals $R^3$ are present in the compound of the general formula (II), these can be identical or different.

Preference is given to the radicals $R^4$ each being, independently of one another, linear or branched, optionally functionalized $C_1$-$C_{30}$-alkyl, particularly preferably $C_1$-$C_{20}$-alkyl, very particularly preferably $C_1$-$C_{12}$-alkyl. In a preferred embodiment, $R^4$ is linear or branched, unfunctionalized $C_1$-$C_{30}$-alkyl, particularly preferably $C_1$-$C_{20}$-alkyl, very particularly preferably $C_1$-$C_{12}$-alkyl. Examples of linear or branched $C_1$-$C_{12}$-alkyl radicals are methyl, ethyl, propyl, in particular n-propyl, isopropyl, butyl, in particular n-butyl, isobutyl, tert-butyl, pentyl, in particular n-pentyl, isopentyl, tert-pentyl, hexyl, in particular n-hexyl, isohexyl, tert-hexyl, heptyl, in particular n-heptyl, isoheptyl, tert-heptyl, octyl, in particular n-octyl, isooctyl, tert-octyl, nonyl, in particular n-nonyl, isononyl, tert-nonyl, decyl, in particular n-decyl, isodecyl, tert-decyl, undecyl, in particular n-undecyl, isoundecyl, tert-undecyl, or dodecyl, in particular n-dodecyl, isododecyl, tert-dodecyl.

Further preference is given to the radicals $R^4$ each being, independently of one another, linear or branched, optionally functionalized $C_2$-$C_{30}$-alkenyl, particularly preferably $C_2$-$C_{20}$-alkenyl, very particularly preferably $C_2$-$C_{12}$-alkenyl. Examples of alkenyl radicals which are particularly preferred according to the invention are ethenyl (vinyl), propenyl, in particular n-propenyl, isopropenyl, butenyl, in particular n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl, tert-dodecenyl.

Further preference is given to the radicals $R^4$ each being, independently of one another, linear or branched, optionally functionalized $C_2$-$C_{30}$-alkynyl, particularly preferably $C_2$-$C_{20}$-alkynyl, very particularly preferably $C_2$-$C_{12}$-alkynyl. Examples of alkynyl radicals which are particularly preferred according to the invention are ethynyl, propynyl, in particular n-propynyl, isopropynyl, butynyl, in particular n-butynyl, isobutynyl, tert-butynyl, pentynyl, in particular n-pentynyl, isopentynyl, tert-pentynyl, hexynyl, in particular n-hexynyl, isohexynyl, tert-hexynyl, heptynyl, in particular n-heptynyl, isoheptynyl, tert-heptynyl, octynyl, in particular n-octynyl, isooctynyl, tert-octynyl, nonynyl, in particular n-nonynyl, isononynyl, tert-nonyl, decynyl, in particular n-decynyl, isodecynyl, tert-decynyl, undecynyl, in particular n-undecynyl, isoundecynyl, tert-undecynyl, or dodecenyl, in particular n-dodecynyl, isododecynyl, tert-dodecynyl.

Further preference is given to the radicals $R^4$ each being, independently of one another, optionally functionalized $C_3$-$C_{20}$-cycloalkyl, particularly preferably $C_3$-$C_{12}$-cycloalkyl, particularly preferably $C_3$-$C_6$-cycloalkyl, for example cyclopropyl, cyclobutyl, cyclopentyl, cyclohexyl.

Further preference is given to the radicals $R^4$ each being, independently of one another, optionally functionalized $C_3$-$C_{20}$-cycloalkenyl, particularly preferably $C_3$-$C_{12}$-cycloalkenyl, very particularly preferably $C_3$-$C_6$-cycloalkenyl, for example cyclopropenyl, cyclobutenyl, cyclopentenyl, cyclohexenyl.

Further preference is given to the radicals $R^4$ each being, independently of one another, optionally functionalized $C_1$-$C_{20}$-heteroalkyl, particularly preferably $C_1$-$C_{12}$-heteroalkyl. The heteroalkyl radicals which are present according to the invention are derived from the abovementioned alkyl radicals, with at least one carbon atom being replaced by a heteroatom selected from among N, O, P and S.

Further preference is given to the radicals $R^4$ each being, independently of one another, optionally functionalized $C_5$-$C_{22}$-aryl, particularly preferably $C_5$-$C_{12}$-aryl. Examples of aryl radicals which are preferred according to the invention are phenyl, naphthyl, biaryls.

Further preference is given to the radicals $R^4$ each being, independently of one another, optionally functionalized $C_6$-$C_{23}$-alkylaryl, particularly preferably $C_6$-$C_{13}$-alkylaryl. An example of an alkylaryl radical which is preferred according to the invention is benzyl.

Further preference is given to the radicals $R^4$ each being, independently of one another, optionally functionalized $C_6$-$C_{23}$-arylalkyl, particularly preferably $C_6$-$C_{13}$-arylalkyl. Examples of arylalkyl radicals which are preferred according to the invention are tolyl, xylyl, propylbenzyl, hexylbenzyl.

Further preference is given to the radicals $R^4$ each being, independently of one another, optionally functionalized $C_5$-$C_{22}$-heteroaryl, particularly preferably $C_5$-$C_{12}$-heteroaryl.

$R^4$ can, in one embodiment, be —$OR^{18}$, where $R^{18}$ has the abovementioned meanings. In one possible embodiment, possible and preferred embodiments of $R^{18}$ correspond, independently of one another, to the possible and preferred embodiments mentioned for $R^2$. In this embodiment, $R^{18}$ is very particularly preferably selected from among methyl, ethyl, hexyl, octyl, decyl, dodecyl. When $R^4$ is —$OR^{18}$, crosslinked siloxane structures are formed in the modification of the particle surface.

In a further preferred embodiment of the present invention, $R^4$ is a unit of the general formula

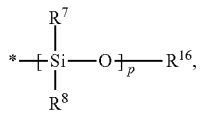

where $R^7$, $R^8$, $R^{16}$ and p have the above-mentioned meanings.

The preferred embodiments of $R^7$ and $R^8$ correspond, independently of one another, to the possible and preferred embodiments mentioned for $R^2$. $R^7$ and $R^8$ are very particularly preferably selected independently from among methyl, ethyl, hexyl, octyl, decyl, dodecyl.

In one possible embodiment, possible and preferred embodiments of $R^{16}$ correspond, independently of one another, to the possible and preferred embodiments mentioned for $R^2$. In this embodiment, $R^{16}$ is very particularly preferably selected from among methyl, ethyl.

In a further embodiment of the invention, $R^{16}$ can be a unit of the general formula

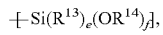

where $R^{13}$, $R^{14}$, e and f have the abovementioned meanings.

In one possible embodiment, possible and preferred embodiments of $R^{13}$ correspond, independently of one another, to the possible and preferred embodiments mentioned for $R^2$. In this embodiment, $R^{13}$ is very particularly preferably selected from among methyl, ethyl, hexyl, octyl, decyl, dodecyl.

In one possible embodiment, possible and preferred embodiments of $R^{14}$ correspond, independently of one another, to the possible and preferred embodiments mentioned for $R^2$. In this embodiment, $R^{14}$ is very particularly preferably selected from among methyl, ethyl.

The indices e are each, independently of one another, 0, 1 or 2, preferably 0.

f is 3-e, i.e. f can assume the values 1, 2 or 3, with 3 being preferred.

The abovementioned radicals $R^4$ can optionally be functionalized. Suitable functional groups are, for example, selected from among amino, amido, imido, hydroxy, ether, aldehyde, keto, carboxylic acid, thiol, thioether, hydroxamate and carbamate groups. The abovementioned radicals $R^1$ can be simply or multiply functionalized. In the case of multiple functionalization, one functional group can be present a plurality of times or various functional groups are simultaneously present. Furthermore, the radicals mentioned for $R^1$ can also be monosubstituted or polysubstituted by the abovementioned alkyl, alkenyl, alkynyl, aryl, alkylaryl, arylalkyl, heteroalkyl or heteroaryl radicals.

Very particularly preferred radicals $R^4$ are methyl and ethyl.

For the purposes of the present invention, "independently of one another" means that if a plurality of radicals $R^4$ are present in the compound of the general formula (II), these can be identical or different.

What has been said in respect of the radicals $R^3$ and $R^4$ applies, independently, to the radicals $R^5$, $R^6$, $R^7$ and $R^8$. Particularly preferred radicals $R^5$, $R^6$, $R^7$ and $R^8$ are selected independently from among methyl and ethyl.

In the compound of the general formula (I), n is generally 1, 2 or 3. n in the compound of the general formula (I) is preferably 1 or 2. n in the compound of the general formula (I) is particularly preferably 1.

The present invention therefore preferably provides the mixture of the invention in which n in the compound of the general formula (I) is 1 or 2, particularly preferably 1.

In the polysiloxanes of the general formula (II) m, o and p are each, independently of one another, generally from 1 to 500, preferably from 1 to 50, particularly preferably from 1 to 20.

Compounds of the general formula (I) which are particularly preferred according to the invention are selected from the group consisting of [2-(3-cyclohexenyl)ethyl]trimethoxysilane, trimethoxy(7-octen-1-yl)silane, isooctyltrimethoxysilane, N-(3-triethoxysilylpropyl)methoxyethoxyethoxyethylcarbamate, N-(3-triethoxy-silylpropyl)methoxyethoxyethoxyethylcarbamate, 3-(methacryloyloxy)propyltrimethoxysilane, allyltrimethoxysilane, 3-acryloxypropyltrimethoxysilane, 3-(methacryloyloxy)-propyltriethoxysilane, 3-(methacryloyloxy)propylmethyldimethoxysilane, 3-(acryloyloxy-propyl)methyldimethoxysilane, 3-(methacryloyloxy)propyldimethylethoxysilane, 3-(methacryloyloxy)propyldimethylethoxysilane, vinyldimethyl-5-ethoxysilane, phenyl-trimethoxysilane, n-octyltrimethoxysilane, dodecyltrimethoxysilane, isooctyltrimethoxy-silane, octadecyltrimethoxysilane, propyltrimethoxysilane, hexyltrimethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxy-silane, vinyltritbutoxysilane, vinyltrisisobutoxysilane, vinyltriisopropenoxysilane, vinyltris(2-methoxyethoxy)silane, styrylethyltrimethoxysilane, mercaptopropyl-trimethoxysilane, 3-glycidoxypropyltrimethoxysilane, heptamethyl(2-[tris(2-methoxyethoxy)silyl]ethyl)trisiloxane and mixtures thereof.

One class of polysiloxanes of the general formula (II) respectively polysiloxanes of general formula (I) comprising groups of general formula (IIa) which is preferred according to the invention is polydimethylsiloxanes which can have, for example, methoxy and/or ethoxy end groups.

The reaction of the abovementioned metal oxide or semimetal oxide particles with the compounds of the general formula (I) or the polysiloxanes of the general formula (II) respectively polysiloxanes of general formula (I) comprising groups of general formula (IIa) can be carried out by processes known to those skilled in the art, for example contacting of the substrates in a solvent, for example toluene or water, at a temperature in the range from room temperature to the boiling point of the solvent. After conventional work-up, the reaction product of metal oxide or semimetal oxide particles and compounds of the general formula (I) or polysiloxanes of the general formula (II) respectively polysiloxanes of general formula (I) comprising groups of general formula (IIa) can be obtained.

Here, hydrolysis of the silicon ether (Si—OR+$H_2O$) to the silanol (Si—OH+ROH) occurs in a first step, followed in a second step by condensation of the surface hydroxyl groups with the silanol to give the product (Si—OH+M-OH→Si—O-M+$H_2O$). According to the invention, only $SiOR^2$ can be hydrolyzed in the above-mentioned silicon-comprising compounds; $R^1$, $R^3$ and all further radicals mentioned cannot be hydrolyzed.

Hydrolysis of alkoxysilanes can be accelerated by decreasing the pH-value of the solution by addition of acids. In one embodiment this step can be conducted before the silanes are contacted with the metal- or semi-metal oxide particles, or, in a second embodiment, afterwards. In the later case, pH-value and acid are selected in a way that oxide particles are not attacked thereby. Preferred is the use of acetic acid or nitric acid. Further preferred is adjustment of the pH-value of 3 to 4. Under certain circumstances, the pH-value of the reaction mixture changes during reaction. In this case, it is useful to adjust the pH-value for completion of surface fixation to 3 to 4, again. A further acceleration of the reaction can be achieved by working at increased temperature, preferably near the boiling point of the solvent.

After obtaining the desired reaction degree, the solid can be separated from the solution by filtration or similar processes, known to the skilled artisan, or the solution is, preferably, dried under using of decreased pressure and/or increased temperature.

If desired, the condensation degree of the hydroxy species and therewith the cross-linking is increased afterwards, by a temperature treatment. It has to be noted that this temperature should be selected in a way that all reaction partners are stable under these given conditions. In a particularly preferred embodiment, temperatures above room temperature, for example up to 200° C., particularly up to 160° C. Water that is formed in the condensation is preferably additionally removed from the reaction zone.

A further possibility to contact the silane reagent with the metal- or semi-metal oxide particles is by spraying of a solution of the reagent onto the solid. Preferably, alkoxysilanes that are already in solution are transferred into silanoles. An advantage of this embodiment is, that less solvent has to be evaporated in the drying step. Treatment after drying can be conducted as mentioned above.

The present invention therefore also relates to a process for the preparation of a surface-modified particle as defined above by contacting the metal- or semi-metal oxide particle, which is to be modified with a compound of general formula (I) or with polysiloxanes of general formula (I), comprising groups of general formula (IIa), as defined above.

The present invention preferably relates to the process according to the present invention, wherein the contacting of the metal- or semi-metal oxide particle that is to be modified with the compound of general formula (I) or with polysiloxanes of general formula (I), comprising groups of general formula (IIa) as defined above, is conducted by spraying.

The present invention preferably relates to the process according to the present invention, wherein the reaction is accelerated by adjusting of the pH-value, preferably by addition of acid.

The present invention preferably relates to the process according to the present invention, wherein a temperature treatment is conducted after drying of the products, preferably at up to 160° C.

The present invention preferably relates to the process according to the present invention, wherein the contacting is conducted by spraying the compounds of general formula (I) or the polysiloxanes of general formula (I) comprising groups of general formula (IIa) as defined above, onto the metal- or semi-metal oxide particle that is to be modified.

The stable mixture of the invention comprises at least one solvent, at least one surface-active substance or a mixture thereof in addition to the abovementioned functionalized metal oxide or semimetal oxide particles.

According to the invention, it has surprisingly been found that the reaction products according to the invention, i.e. the surface-functionalized metal oxide or semimetal oxide particles, are particularly stable in mixtures with solvents and/or surface-active compounds, i.e. no detachment of the silicon compounds bound to the surface occurs.

The at least one solvent present in the mixture of the invention is preferably selected from the group consisting of aromatic hydrocarbons, for example benzene, toluene, xylene, alcohols, for example methanol, ethanol, propanols such as n-propanol, isopropanol, butanols such as n-butanol, isobutanol, tert-butanol, ethers such as diethyl ether, methyl tert-butyl ether, isobutyl tert-butyl ether, cyclic ethers such as tetrahydrofuran, dioxane, esters, cyclic esters, alkanes such as hexane, cycloalkanes such as cyclohexane, olefins, cycloolefins, water and mixtures thereof. If mixtures of solvents are used according to the invention, preference is given to using solvents which are completely miscible with one another, i.e. form a single phase on mixing.

The present invention therefore preferably provides the mixture of the invention in which the at least one solvent is selected from the group consisting of aromatic hydrocarbons, preferably benzene, toluene, xylene, alcohols, for example methanol, ethanol, propanols such as n-propanol, isopropanol, butanols such as n-butanol, isobutanol, tert-butanol, ethers such as diethyl ether, methyl tert-butyl ether, isobutyl-tert-butyl ether, cyclic ethers such as tetrahydrofuran, dioxane, esters, cyclic esters, alkanes such as hexane, cycloalkanes such as cyclohexane, olefins, cycloolefins, water and mixtures thereof.

In a preferred embodiment, the mixture of the invention is used in processes in which the surface-modified particles are brought into contact with particularly large amounts of solvents.

The mixture of the invention generally has a solids content of up to 70% by weight, preferably up to 60% by weight. The content of at least one solvent in the mixture of the invention is therefore generally at least 30% by weight, preferably at least 40% by weight, i.e. in general from 30 to 99.9% by weight, preferably from 40 to 99.9% by weight, of solvent. According to the invention, the solids content is the content of particles which have been modified on the surface according to the invention and any further solids present.

The at least one surface-active substance present in the mixture of the invention is preferably selected from the group consisting of nonionic, anionic, cationic or zwitterionic surfactants and mixtures thereof.

Preferred examples of nonionic surfactants are fatty alcohol polyglycol ethers, in particular fatty alcohol polyethylene glycol ethers.

Preferred examples of anionic surfactants are alkylbenzenesulfonates, secondary alkanesulfonates, α-olefinsulfonates, fatty alcohol sulfates or fatty alcohol ether sulfates.

Preferred examples of cationic surfactants are stearyltrimethylammonium salts.

Preferred examples of zwitterionic surfactants are sultaines, fatty acid amidoalkylhydroxysultaine or alkyl betaines.

Particularly preferred surface-active substances are sodium alkylphenol ether sulfates.

The at least one surface-active substance is generally present in the mixture of the invention in an amount of from 0.001 to 20% by weight, preferably from 0.01 to 15% by weight, particularly preferably from 0.1 to 10% by weight, in each case based on the total mixture. If at least one surface-active substance is present according to the invention, the abovementioned amount of at least one solvent is modified accordingly.

The surface-functionalized metal oxide or semimetal oxide particles are generally present in the mixture of the invention in an amount of from 0.1 to 70% by weight, preferably from 0.1 to 60% by weight.

If further solids are optionally present in the mixture of the invention, the abovementioned amount of surface-functionalized metal oxide or semimetal oxide particles is modified accordingly.

In all possible embodiments, the amounts of surface-functionalized metal oxide or semimetal oxide particles, at least one solvent, optionally present surface-active substances and optionally present further solids add up to 100% by weight.

Apart from the functionalized particles, the at least one solvent and/or the at least one surface-active substance, the mixture of the invention can comprise further components, for example oxidic or metallic solids and further hydrophobic components. The sum of the amounts of the components present in the mixture of the invention in each case add up to 100% by weight.

The mass ratio of solvent to modified particles in the mixture of the invention is generally greater than 500, preferably 1000, particularly preferably greater than 5000, very particularly preferably greater than 10 000.

For the purposes of the present invention, the term "stable mixture" means that the surface-functionalized metal oxide or semimetal oxide particles present in the mixture of the invention are not changed in the mixture, i.e. the silyl groups present on the surface are not detached from the surface of the metal oxide or semimetal oxide particles, for example by hydrolysis, so that the mixture of the invention as a whole does not change or changes only slightly. That a mixture comprising surface-modified particles is stable for the purposes of the present invention can be demonstrated, for example, by the fact that such particles which are in contact with solvents and/or surface-active substance in a mixture according to the invention remain chemically and/or physically unchanged. This can, for example, be determined by elemental analysis or determination of the hydrophobic properties, for example by determination of the ability to float or the contact angle.

The present invention also provides a process for treating surface-modified particles according to the invention with at least one solvent, wherein the mass ratio of solvent to modified particle is greater than 500.

As regards the surface-modified particles and the solvents, what has been said above in respect of the mixture according to the invention applies to the process of the invention.

In the process of the invention, the mass ratio of surface-modified particle and the at least one solvent is generally greater than 500, preferably greater than 1000, particularly preferably greater than 5000, very particularly preferably greater than 10 000.

In this process of the invention, the surface-modified particles according to the invention are brought into contact, i.e. treated, with a relatively large amount of solvent. Corresponding systems according to the invention in which this treatment can be carried out are, for example, flowing systems in which the surface-modified particles of the invention are brought into contact in, for example, continuous processes with further substances, particles, materials, etc., for example continuous processes for agglomeration with further substances, particles, materials, etc., in solution or dispersion. The process of the invention also relates to deagglomeration of agglomerates of the surface-modified particles of the invention and further substances, particles or materials, or of agglomerates of the surface-modified particles with themselves, for example likewise in flowing systems.

The present invention also provides for the use of surface-modified particles according to the invention in systems in which the modified particles are brought into contact with at least one solvent, wherein the mass ratio of solvent to modified particles is greater than 500.

As regards the surface-modified particles and the solvents, what has been said above in respect of the mixture of the invention applies.

The mass ratio of surface-modified particle and the at least one solvent is generally greater than 500, preferably greater than 1000, particularly preferably greater than 5000, very particularly preferably greater than 10 000.

In this use according to the invention, the surface-modified particles of the invention are brought into contact with a relatively large amount of solvent. Corresponding systems according to the invention in which this contacting can be carried out are, for example, flowing systems in which the surface-modified particles of the invention are brought into contact in, for example, continuous processes with further substances, particles, materials, etc., for example continuous processes for agglomeration with further substances, particles, materials, etc., in solution or dispersion. The use according to the invention also relates to deagglomeration of agglomerates of the surface-modified particles of the invention and further substances, particles or materials, or of agglomerates of surface-modified particles with themselves, for example likewise in flowing systems.

The present invention also provides for the use of surface-modified particles according to the invention, in particular magnetic particles, in agglomeration-deagglomeration cycles.

In this use too, what has been said in respect of the mixture of the invention applies to the surface-modified particles and the solvents.

According to the invention, an agglomeration-deagglomeration cycle is a process in which the surface-functionalized particles of the invention, in particular magnetic particles, are brought into contact with themselves or other particles, substances, materials, etc., in solution or dispersion and agglomerate as a result of hydrophobic interaction, ionic forces, van der Waals interactions and/or other attractive forces. These agglomerates are then processed in further processes, for example separated from other components and/or the solution or dispersion. After this treatment, the agglomerates are then separated again, i.e. deagglomerated, so that the surface-functionalized particles and the other particles, substances, materials, etc., are again present separately (deagglomeration). Examples of agglomeration-deagglomeration cycles which are preferred according to the invention are chemical or biological test methods or separation processes, decontamination of (heavy metal-)contaminated earth, water purification, recycling of electrical/electronic scrap or gravity separation.

In chemical or biological test methods or separation processes, use is made of, for example, specifically modified magnetic nanoparticles which have anchor groups for a specific antigen or virus, e.g. borrelia, HIV, hepatitis, on their surface. These specific anchor groups correspond, in particular, to the abovementioned group $R^1$ which has a structure corresponding to the respective separation or test task, for example as a result of the presence of the abovementioned functional groups. Bonding of these antigens/viruses to the modified particle surface (agglomeration) enables these constituents to be separated off from a solution by means of magnetic separation and thus detected. The functionalized magnetic particles are then recycled by means of surfactants which again release the electrostatic, adhesive or van der Waals interaction between functionalized magnetic particle and antigen/virus (deagglomeration). In this way, the functionalized magnetite particles produced in an elaborate way can be reused.

The modified particles of the invention, in particular magnetic particles, can be used in water purification. Here, for example, it is possible to use functionalized magnetite particles which remove organic constituents, suspended materials or fat droplets from the water by effecting hydrophobic agglomeration between the functionalized magnetite particle and the hydrophobic contaminant. These hydrophobic agglomerates can be separated off by magnetic separation. In order that water purification is economical, it is useful to "unload" the hydrophobic magnetite particles from the contaminant again and return them to the circuit. This "unloading" can once again be affected by deagglomeration using a specific surface-active substance (surfactant) and/or by means of a specific solvent or solvent mixture.

Recycling of electrical/electronic scrap can, for example, be carried out by magnetic recovery of materials of value (Ir, Pt, Ru) from electrical/electronic scrap, once again preferably using modified magnetite particles which, after hydrophobicization of the materials of value to be separated, can agglomerate with these and be separated off. After the agglomerates have been separated off, they are deagglomerated again so that the modified magnetic particles can be reused.

A further example is gravity separation, e.g. by means of cyclones known to those skilled in the art. In this way, relatively dense constituents can be separated off from less dense constituents by means of a gravity separation. If the densities of the individual components differ only slightly, e.g. Pt-doped hematite and undoped hematite, the density of the component to be separated off can be increased by agglomeration with a further component. Here, for example, the Pt-doped hematite component is hydrophobicized according to the invention to give modified particles, so that addition of hydrophobicized barium sulfate gives an agglomerate of the modified hematite and barium sulfate which has a greater density difference from the undoped hematite. After the agglomerate has been separated off, it can be deagglomerated again.

The present invention therefore also preferably provides for the use according to the invention in which the agglomeration-deagglomeration cycle is a chemical or biological test method or separation process, water purification, purification of (heavy metal-) polluted earth, recycling of electrical/electronic scrap or gravity separation.

An advantage of the invention is that the particles which have been surface-modified according to the invention are stable under the conditions prevailing in agglomeration and especially deagglomeration and can therefore preferably be reused.

EXAMPLES

Example 1

General Methods

Example 1.1

Repeated Treatment of the Solid with Surfactant Solution 10 g of solid are stirred in 1 l of a 0.2% strength by weight solution of Lutensit A-ES from BASF SE (mixture of sodium alkylphenol ether sulfates) in water for 2 hours at room temperature. The solid is subsequently filtered off and washed with 1 l of water, 100 ml of ethanol and 100 ml of acetone. The filter cake is dried at 120° C. under reduced pressure for 4 hours. Samples are subsequently taken for analysis. The remaining product is used for the renewed washing tests.

Example 1.2

Rapid Test for Ability to Float on Water 3 ml of water are placed in a 5 ml test tube. The solid to be examined is subsequently carefully placed on the surface of the water by means of a spatula. The solid in the test tube is subsequently observed to see whether the solid sinks or remains afloat. In the case of floating solids, the closed vessel is shaken for 10 s. The solid in the test tube is subsequently observed to see whether the solid floats again or remains under water.

Example 1.3

Contact Angle Measurement

Contact Angle Measurement on Powders:

Contact angles are measured using a standard instrument (Dropshape Analysis Instrument, Kruss DAS 10). A silhouette of the drop is recorded by means of a CCD camera and the drop shape is determined by computer-aided image analysis. The measurements are, unless indicated otherwise, carried out as described in DIN 5560-2.

a) Production of a Homogeneous Powder Layer

The magnetite powder is applied as an appropriately 1 mm thick layer onto a 100 µm thick BASF Acronal V215 adhesive dispersion on a PET film. Using a spatula, the powder is pressed into the adhesive and excess material which does not adhere is removed by shaking. Finally, remaining loose material is removed by blowing purified nitrogen under pressure over the specimen. This method gives a clean, homogeneous powder surface over the total area of the substrate of 75 mm×25 mm.

Powder surfaces normally display a certain roughness and contact angle or the measurement thereof are sensitive to this roughness. A direct comparison of the hydrophobicity can therefore be carried out only on powders having the same particle size distribution and particle shape. Careful surfaces analyses using ToF-SIMS have shown that the surface of the powder layer produced by this method has no traces of adhesive and is representative of the powder.

b) Dynamic, Progressive Contact Angle Measurement

One milliliter of water is placed as a drop on the surface and 2 µl/min of water are continuously added. 20 µl of liquid volume are added continuously in this way. Starting from a minimal volume of about 3 µl, contact angles are measured while the needle of the syringe used for introduction remains in the drop. Contour measurements are carried out at a rate of about 0.5 Hz and are evaluated by means of a tangent method in order to determine the contact angle directly at the three-phase contact line. These contact angles are averaged over time, and five progressive drops are measured at various positions for each sample and the average value together with a standard deviation is determined.

Example 1.4

Recycling Experiments

An experiment is carried out on the use of magnetite hydrophobicized according to the respective example as reusable carrier for the decontamination of (heavy metal-)contaminated earth. For this purpose, 3 g of magnetite were dispersed in a system comprising 100 g of a sand mixture (solids content: 1% by weight). This sand mixture comprises 99% by weight of inorganic siliceous constituents (e.g. feltspars, mica, iron pyrites) and 1% by weight of a specific hydrophobicized inorganic As-comprising contaminant (Enargite). Hydrophobicization of this inorganic contaminant is carried out using butylxanthate. After vigorous mixing of the hydrophobicized magnetite with this sand mixture, the arsenic component is separated off by means of hydrophobic flocculation with the magnetite. The hydrophobic constituents are collected and treated with a 0.1% strength by weight solution of a surfactant (Lutensit A-ES from BASF SE). In a subsequent magnetic separation step, the magnetic constituents are separated from the nonmagnetic As-comprising impurities. The hydrophobic magnetite is washed with a 1:1 mixture of water and EtOH, filtered off and remixed with a freshly produced sand mixture. The process is repeated a total of ten times.

Example 2

Production of Hydrophobicized Magnetite

Example 2.1

Magnetic Pigment 345 from BASF SE Silanized with $^{n}OctSi(OMe)_3$ (According to the Invention)

Synthesis: 10 g of magnetite pigment 345 (magnetite $Fe^{II}(Fe^{III})_2O_4$) from BASF SE are added to a solution of 370 mg of $^{n}OctSi(OMe)_3$ (97% strength, from ABCR) in 30 ml of toluene. 1 ml of 25% strength acetic acid is then added to the solution. After 4 hours under reflux, the solid is filtered off and washed with 5 ml of acetone and 1 l of distilled water. The product is dried overnight at 120° C. under reduced pressure. The dried product is, after preliminary comminution, brushed through an analytical sieve (400 μm) and thus deagglomerated and homogenized.
Analysis:
Floatation test: fresh solid and solid which has been washed ten times float equally well on water (also after shaking under);
Elemental analysis: fresh: 0.12% of C, 0.06% of Si, washed ten times: 0.12% of C, 0.06% of Si;
Contact angle: fresh 152°, washed ten times 146°;
Recycling test: When the yield of the As component is detected, the yield of 95% in the first cycle drops to only 91% in the tenth cycle when using the $^{n}OctSi(OMe)_3$-silanized magnetic pigment 345 from BASF SE.

Example 2.2

$^{n}HexSi(OMe)_3$-Silanized Magnetic Pigment 345 from BASF SE (According to the Invention)

Synthesis: The synthesis is carried out according to the scheme described in example 2.1. However, 330 mg of $^{n}HexSi(OMe)_3$ (97% strength, from ABCR) are used as silanization reagent.
Analysis:
Floatation test: fresh solid and solid which has been washed ten times float equally well on water (also after shaking under);
Elemental analysis: fresh: 0.08% of C, 0.05% of Si, washed ten times: 0.07% of C, 0.05% of Si;
Contact angle: fresh 156°, washed ten times 152°

Example 2.3

$^{n}BuSi(OMe)_3$-Silanized Magnetic Pigment 345 from BASF SE (According to the Invention)

Synthesis: The synthesis is carried out according to the scheme described in example 2.1. However, 290 mg of $^{n}BuSi(OMe)_3$ (97% strength, from ABCR) are used as silanization reagent.
Analysis:
Floatation test: fresh solid and solid which has been washed ten times float equally well on water (also after shaking under);
Elemental analysis: fresh: 0.06% of C, 0.05% of Si, washed ten times: 0.07% of C, 0.05% of Si;
Contact angle: fresh 146°, washed ten times 133°;

Example 2.4

$^{n}OctSi(OMe)_3$-Silanized Magnetic Pigment 345 from BASF SE (According to the Invention)

Synthesis: The synthesis is carried out according to the scheme described in example 2.1. However, water is used instead of toluene as solvent. This is brought to a pH of 3.5 by means of 25% strength acetic acid.
Analysis:
Floatation test: fresh solid and solid which has been washed ten times float equally well on water (also after shaking under);
Elemental analysis: fresh: 0.10% of C, 0.06% of Si, washed ten times: 0.10% of C, 0.04% of Si;
Contact angle: fresh 155°, washed ten times 148°;
Recycling test: When the yield of the As component is detected, the yield of 94% in the first cycle drops to only 92% in the tenth cycle when using the $^{n}OctSi(OMe)_3$-silanized magnetic pigment 345.

Example 2.5

$^{n}OctSi(OMe)_3$ Silanized Magnetic Pigment 345 of BASF SE (According to the Invention)

Synthesis: A solution of 370 mg $^{n}OctSi(OMe)_3$ (97% by weight, ABCR) in 5 mL water is adjusted to pH 3.5 with 25% by weight acidic acid and stirred for 60 minutes at room temperature. Afterwards, the solution is sprayed onto 10 g magnetic pigment 345 (magnetite $Fe^{III}(Fe^{III})_2O_4$) of BASF SE, whereat the solid is constantly stirred. The product is dried at 120° C. for 2 hours in vacuum. Afterwards, the reaction is completed at 160° C. for 12 hours. The obtained product is primed after premilling through an analysis sieve (400 μm) and is therewith deagglomerated and homogenized.
Analytic:
Floatation test: fresh solid and solid which has been washed ten times float equally well on water (also after shaking under);
Contact angle: fresh 151°, washed ten times 154°.

Example 3

Comparative Examples

Comparative Example 3.1

Commercial, Hydrophobic Magnetite Bayoxide E8707 H from Lanxess (not According to the Invention)

Analysis:
Floatation test: fresh solid floats on water even after shaking under, while solid which has been washed twice no longer floats;

Elemental analysis: fresh: 0.10% of C, 0.05% of Si, washed ten times: 0.03% of C, 0.01% of Si;

Contact angle: fresh 158°, washed ten times 116°

Recycling: Comparative tests using a previously hydrophobicized magnetite from Lanxess (product: Bayoxide E8707 H) display a dramatic loss in yield of over 40% after only the fourth cycle. The experiments using this product are then stopped.

Comparative Example 3.2

$^n$OctMe$_2$SiCl-Silanized Magnetic Pigment 345 from BASF SE (not According to the Invention)

Synthesis: Under a protective atmosphere, 10 g of magnetic pigment 345 from BASF SE are suspended in 20 ml of toluene. The suspension is heated to 70° C., and 0.3 g of $^n$OctMe$_2$SiCl (97% strength, from ABCR) are then added. The reaction mixture is subsequently maintained at 70° C. for 4 hours while stirring. The solid is subsequently filtered off, washed firstly with 50 ml of toluene, then 50 ml of methanol and finally water until the washings are free of chloride. The product is dried at 120° C. under reduced pressure for 4 hours. The dried product is, after preliminary comminution, brushed through an analytical sieve (400 μm) and thus deagglomerated and homogenized.

Analysis:

Floatation test: solid floats on water (even after shaking under), while solid washed once no longer floats on water;

Elemental analysis: fresh: 0.10% of C, 0.06% of Si, washed ten times: 0.06% of C, 0.04% of Si;

Contact angle: fresh 148°, washed once 120°, washed ten times 98°

Comparative example 3.3

$^n$BuMe$_2$SiCl-Silanized Magnetic Pigment 345 from BASF SE (not According to the Invention)

Synthesis: The synthesis is carried out according to the scheme described in example 2.1. However, 0.3 g of $^n$BuMe$_2$SiCl (97% strength from ABCR) is used as silanization reagent.

Analysis:

Floatation test: solid floats on water (not after shaking under), while solid washed once no longer floats on water;

Elemental analysis: fresh: 0.09% of C, 0.06% of Si, washed ten times: 0.03% of C, 0.02% of Si;

Contact angle: fresh 103°, washed ten times 89°

Comparative Example 3.4

Magnetic Pigment 345 from BASF SE Hydrophobicized with Octylphosphonic Acid (not According to the Invention)

Synthesis: 8.0 kg of water are placed in an apparatus comprising a 12 l plastic bucket with spout as stirred vessel and a metal stirrer. 2 kg of magnetic pigment 345 from BASF SE are subsequently introduced and the stirring speed of the metal stirrer is selected so that the pigment does not sediment and air is also not drawn in (no head of foam is formed). 12.5 g of n-octylphosphonic acid (OPA, 80% strength) from Albright & Wilson are subsequently added all at once and all the starting materials are mixed in air at room temperature for 1.5 hours. After the end of the stirring time, the suspension is poured on to a porcelain filter (d=24 cm with an MN 85/90 paper filter from Macherey-Nagel). Cracks formed in the filter cake are wiped shut to improve the washing action. The solid is dried overnight at 110° C. in a convection drying oven. The dried product is, after preliminary comminution, brushed through an analytical sieve (400 μm) and thus deagglomerated and homogenized.

Analysis:

Elemental analysis: 0.06% of P in the end product;

Recycling test: Even after the third cycle, only an unsatisfactory yield of the As-comprising impurity of less than 50% is detected. The experiments are subsequently stopped.

The invention claimed is:

1. A stable mixture comprising surface-modified particles which are obtained by reacting metal oxide particles with at least one compound of the general formula (I)

$$R^1{}_n\text{—Si}(OR^2)_{4-n} \quad (I)$$

where $R^1$, $R^2$ and n have the following meanings:

$R^1$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, $R^2$ are each, independently of one another, hydrogen, linear or branched, optionally functionalized $C_1$-$C_{30}$-alkyl, linear or branched, optionally functionalized $C_2$-$C_{20}$-alkenyl, linear or branched, optionally functionalized $C_2$-$C_{20}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl and/or group of the general formula (IIa)

$$\text{—SiR}^1{}_m(OR^2)_{3-m} \quad (IIa)$$

where $R^1$ and $R^2$ independently of one another have the above-mentioned meanings and m is independently of one another 0, 1, 2 or 3, n 1, 2 or 3, and at least one solvent, at least one surface-active substance or a mixture thereof wherein said metal oxide used is an oxide of a metal selected from the group consisting of Mn, Fe, Co, Ni, Cu, combinations thereof.

2. The mixture according to claim 1, wherein the mass ratio of solvent to modified particle is greater than 500.

3. The mixture according to claim 1, wherein n in the compound of the general formula (I) is 1 or 2.

4. The mixture according to claim 1, wherein $R^2$ in the compound of the general formula (I) or in the group of the general formula (IIa) is methyl or ethyl.

5. The mixture according to claim 1, wherein the at least one solvent is selected from the group consisting of aromatic hydrocarbons, alcohols, ethers, cyclic ethers, esters, cyclic esters, alkanes, cycloalkanes, olefins, cycloolefins, water and mixtures thereof.

6. The mixture according to claim 1, wherein the at least one surface-active substance is selected from the group consisting of nonionic, anionic, cationic and zwitterionic surfactants and mixtures thereof.

7. The mixture according to claim 1, wherein the metal oxide is a mixed oxide of a metal selected from the group consisting of Mn, Fe, Co, Ni, Cu, and combinations thereof with at least one alkaline earth metal.

8. The mixture according to claim 1, wherein n in the compound of the general formula (I) is 1.

9. A process for treating surface-modified particles as defined in claim 1 with at least one solvent, wherein the mass ratio of solvent to modified particle is greater than 500.

10. The method of using surface-modified particles as defined in claim 1 in systems in which the modified particles are brought into contact with at least one solvent, wherein the mass ratio of solvent to modified particle is greater than 500.

11. The method of using surface-modified particles as defined in claim 1 in agglomeration-deagglomeration cycles.

12. The method according to claim 11, wherein the agglomeration-deagglomeration cycle is a chemical or biological test method or separation process, decontamination of (heavy metal-)contaminated earth, water purification, recycling of electrical/electronic scrap or gravity separation.

13. Process for the preparation of a surface-modified particle as defined in claim 1 by contacting the metal- or semi-metal oxide particle, which is to be modified with a compound of general formula (I) or with polysiloxanes of general formula (I), comprising groups of general formula (IIa), as defined in claim 1.

14. Process according to claim 13, wherein the contacting of the metal- or semi-metal oxide particle that is to be modified with the compound of general formula (I) or with polysiloxanes of general formula (I), comprising groups of general formula (IIa) as defined in claim 1, is conducted by spraying.

15. Process according to claim 13, wherein the reaction is accelerated by adjusting of the pH-value, preferably by addition of acid.

16. Process according to claim 13, wherein a temperature treatment is conducted after drying of the products, preferably at up to 160° C.

17. Process according to claim 13, wherein the contacting is conducted by spraying the compounds of general formula (I) or the polysiloxanes of general formula (I), comprising groups of general formula (IIa) as defined in claim 1, onto the metal- or semi-metal oxide particle that is to be modified.

* * * * *